Figure 1:
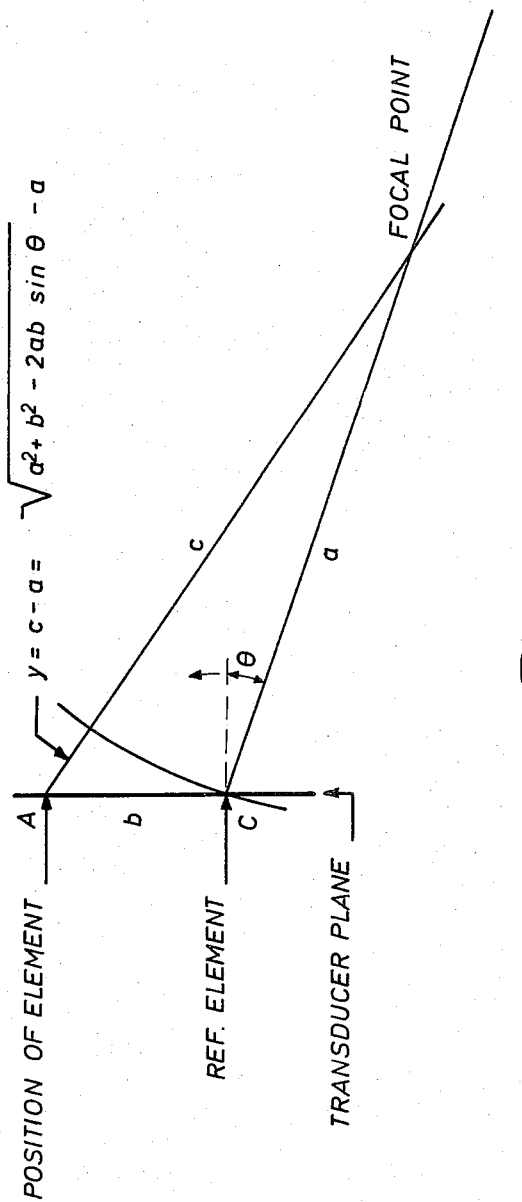

United States Patent [19]

Northeved et al.

[11] 4,309,906
[45] Jan. 12, 1982

[54] APPARATUS FOR PROVIDING AN ULTRASONIC SECTIONAL VIEW

[75] Inventors: Allan Northeved, Bagsvaerd; Knud C. C. Fabrin, Farum, both of Denmark

[73] Assignee: Medicoteknisk Institut, Svejsecentralen, Glostrup, Denmark

[21] Appl. No.: 126,917

[22] Filed: Mar. 3, 1980

Related U.S. Application Data

[63] Continuation of Ser. No. 913,174, Jun. 6, 1978, abandoned.

[30] Foreign Application Priority Data

Jun. 15, 1977 [DK] Denmark .............................. 2642/77
Feb. 15, 1978 [DK] Denmark .............................. 681/78

[51] Int. Cl.³ .............................................. G01N 29/00
[52] U.S. Cl. ........................................ 73/612; 73/625
[58] Field of Search ................. 73/609, 611, 612, 613, 73/614, 625

[56] References Cited

U.S. PATENT DOCUMENTS

3,295,362  1/1967  Wood et al. .......................... 73/613
3,805,597  4/1974  Ohta et al. ............................ 73/612
4,012,952  3/1977  Dory .................................. 73/626 X

FOREIGN PATENT DOCUMENTS

2645738  4/1977  Fed. Rep. of Germany .

Primary Examiner—Charles A. Ruehl
Attorney, Agent, or Firm—Ladas & Parry

[57] ABSTRACT

The present invention relates to an apparatus for providing an ultrasonic sectional view by exciting elements in a plane ultrasonic transducer to form focusing waves. The reflected waves are received and time-coordinated by means of a circuit for each element or each set of elements, whereby the reflected waves are geometrically correctly placed in a visualizing screen. According to the invention the circuits are uniform.

6 Claims, 7 Drawing Figures

APPARATUS FOR PROVIDING AN ULTRASONIC SECTIONAL VIEW

This is a continuation of application Ser. No. 913,174 filed June 6, 1978, now abandoned.

The invention relates to an apparatus for providing an ultrasonic section view, partly by exciting individual elements in a plane ultrasonic transducer to form focusing waves for angular or linear scanning in a focal plane, partly by time-coordinating the signals received by the individual elements, whereby the reflections are selected and geometrically correctly placed on a visualizing screen.

Apparatuses of this type are known, e.g. from U.S. Pat. No. 4,012,952 and from the article "A New Ultrasonic Imaging Technique Employing Two-Dimensional Electronic Beam Steering". However, the circuit controlling the transmitting moments of the individual transducers for focusing the transmitted ultrasonic energy is relatively complicated. As a result the flexibility of the apparatus is limited.

The apparatus according to the invention is characterized by a plurality of uniformly constructed circuits, each circuit comprising an analog calculating circuit, said calculating circuit partly controlling the relative transmitting moments for a transducer element or a set of transducer elements through comparators by means of analog voltages representing the geometric conditions at predetermined moments, and partly controlling the delay of the combined signal received from the same transducer elements by means of an analog memory through a digital system.

As a result the control unit may be composed of a plurality of uniform modules, whereby the number of modules corresponds to the number of transducer elements or to the number of sets of transducer elements.

The modular construction provides partly that the control circuit may have an arbitrary size without being complicated, partly that the control circuit may be manufactured and delivered in arbitrary sizes without demanding a more comprehensive storage capacity, and partly that existing control circuits are easier to extend.

Moreover according to the invention the signals from two transducer elements may be combined into a single signal by means of a phase-summation circuit. As a result the number of control circuits may be reduced.

Furthermore according to the invention the analog memory may be composed of preferably 64 capacitors for scanning of the signal received at 64 equidistant moments, which is sufficient for recreating the recorded signal.

It is according to the invention preferred that the terminals indicating the transducer element position are mutually connected through resistors of one and the same value.

The apparatus according to the invention may furthermore be characterized by the direction indicating terminals being mutually connected through resistors of one and the same value, thus forming a voltage divider. In this manner only one multiplication circuit is necessary. As a result the apparatus is simplified.

Furthermore according to the invention the control of two adjacent transducer elements may be performed by means of an interpolation circuit. As a result the number of modules is reduced.

In an alternative embodiment of the apparatus, said apparatus is according to the invention characterized by the signals from two transducer elements being combined into a single signal by means of a phase-summation circuit of a first type, whereby the outputs of two phase-summation circuits of the first type are connected to a phase-summation circuit of a second type, and the outputs of two phase-summation circuits of the second type are optionally connected to a phase-summation circuit of a third type etc. In this manner each circuit is able to treat signals from at least four transducer elements. As a result the number of circuits is reduced correspondingly.

It is according to the invention preferred that each phase-summation circuit is composed of a delay line in connection with a plurality of cascode amplifiers, whereby the outputs of the delay lines are connected to their respective amplifer.

Furthermore according to the invention it is possible to compensate for attenuations in the delay lines by means of a control voltage being proportional to sine of the angle of incidence of the sound waves scanned by the transducer elements. As a result the fact that the signal transmitted to one input has a longer transmission distance than the signal transmitted to the second input has been compensated as the signal having the long distance of transmission is more amplified than the signal having the short distance of transmission.

Finally according to the invention logarithmic amplifiers may be coupled between the phase-summation circuits, thus placing the signals at a sufficiently uniform level.

Figure 2:
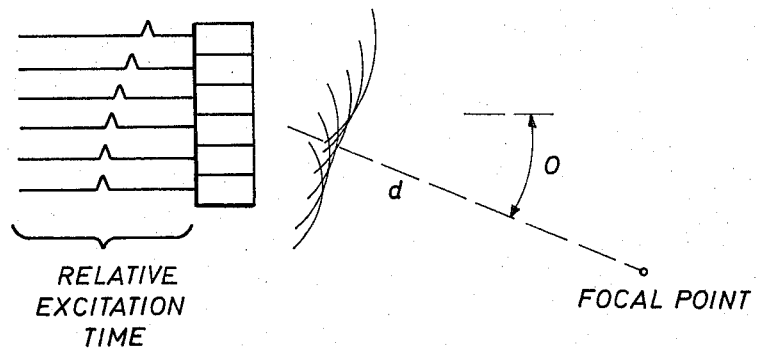
Figure 5:
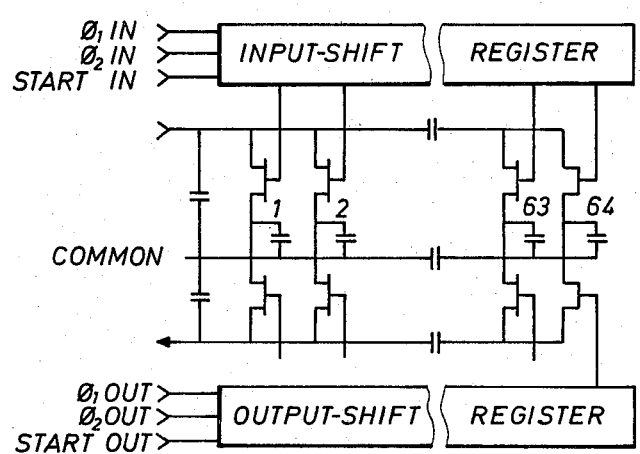
Figure 5:
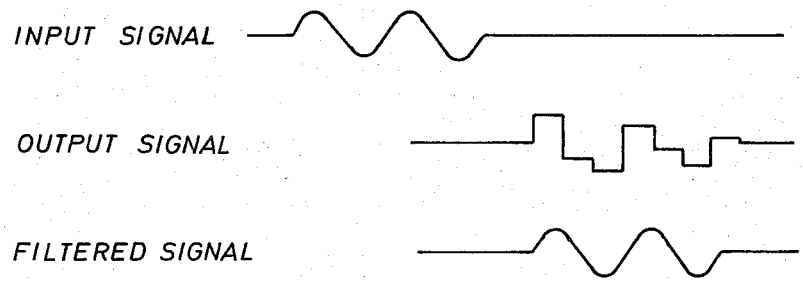
Figure 3:
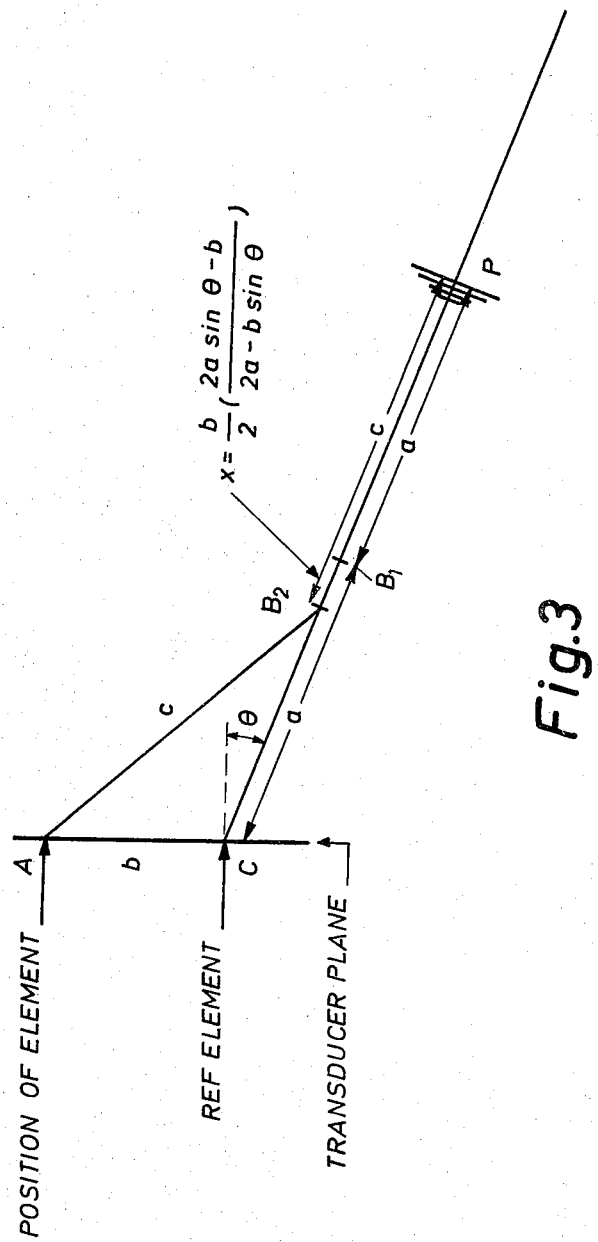
Figure 4:
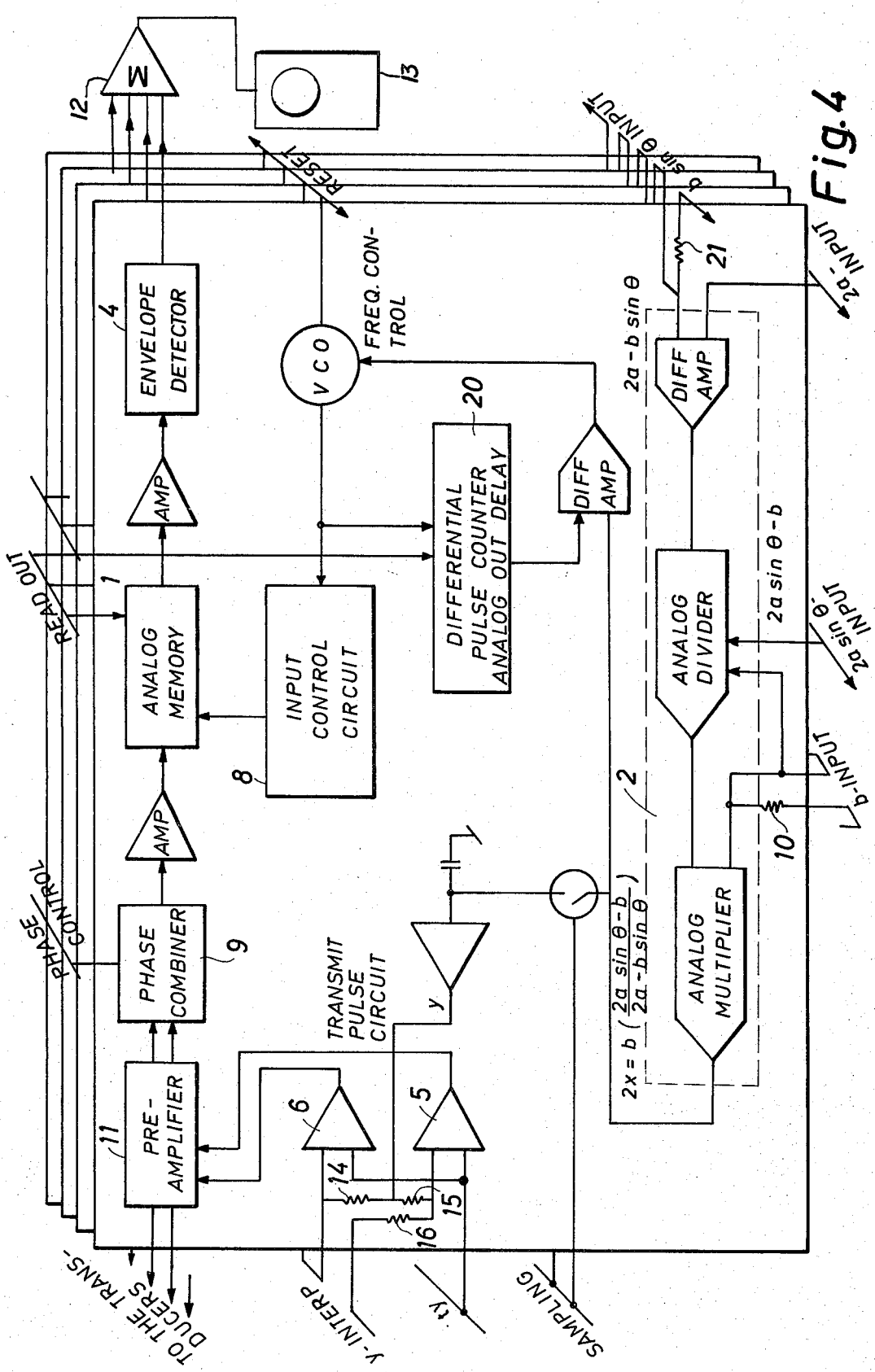
Figure 6:
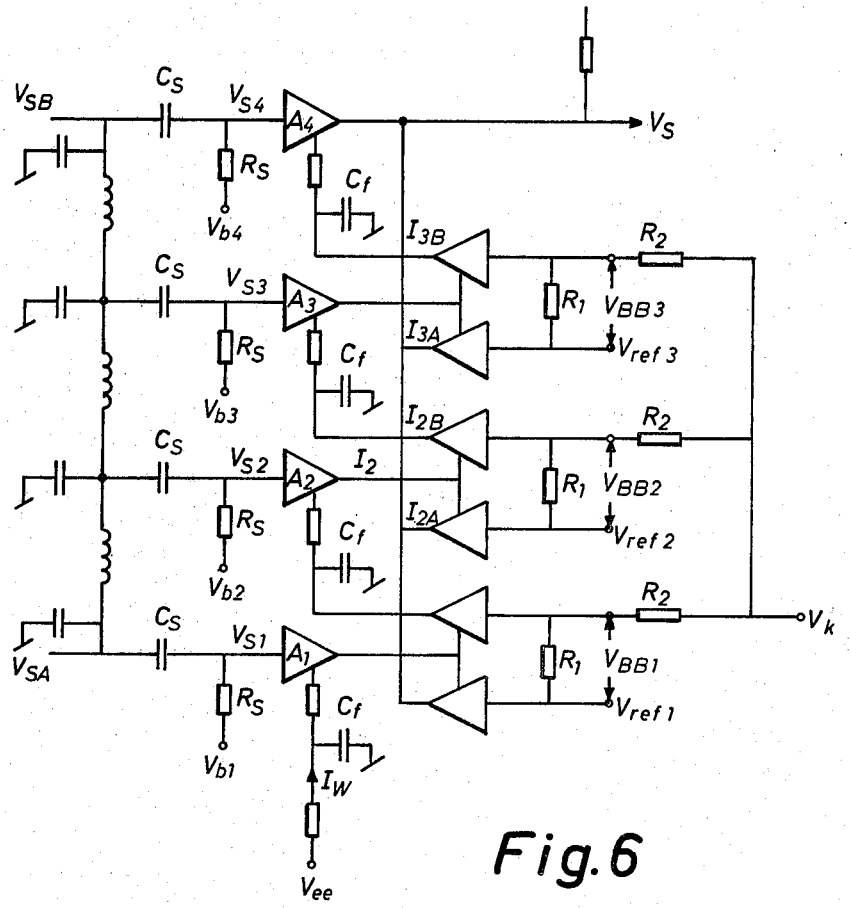
Figure 6:
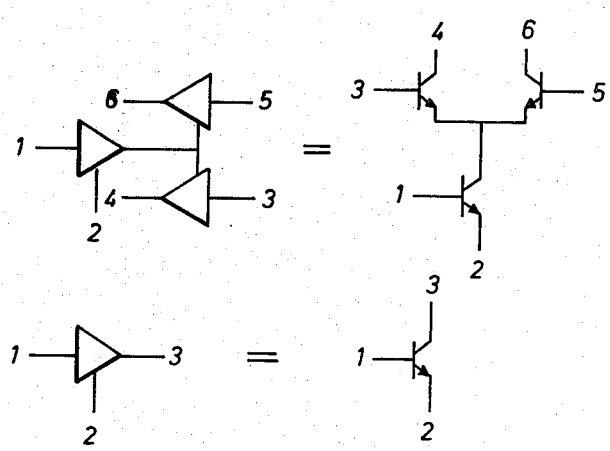
Figure 7:
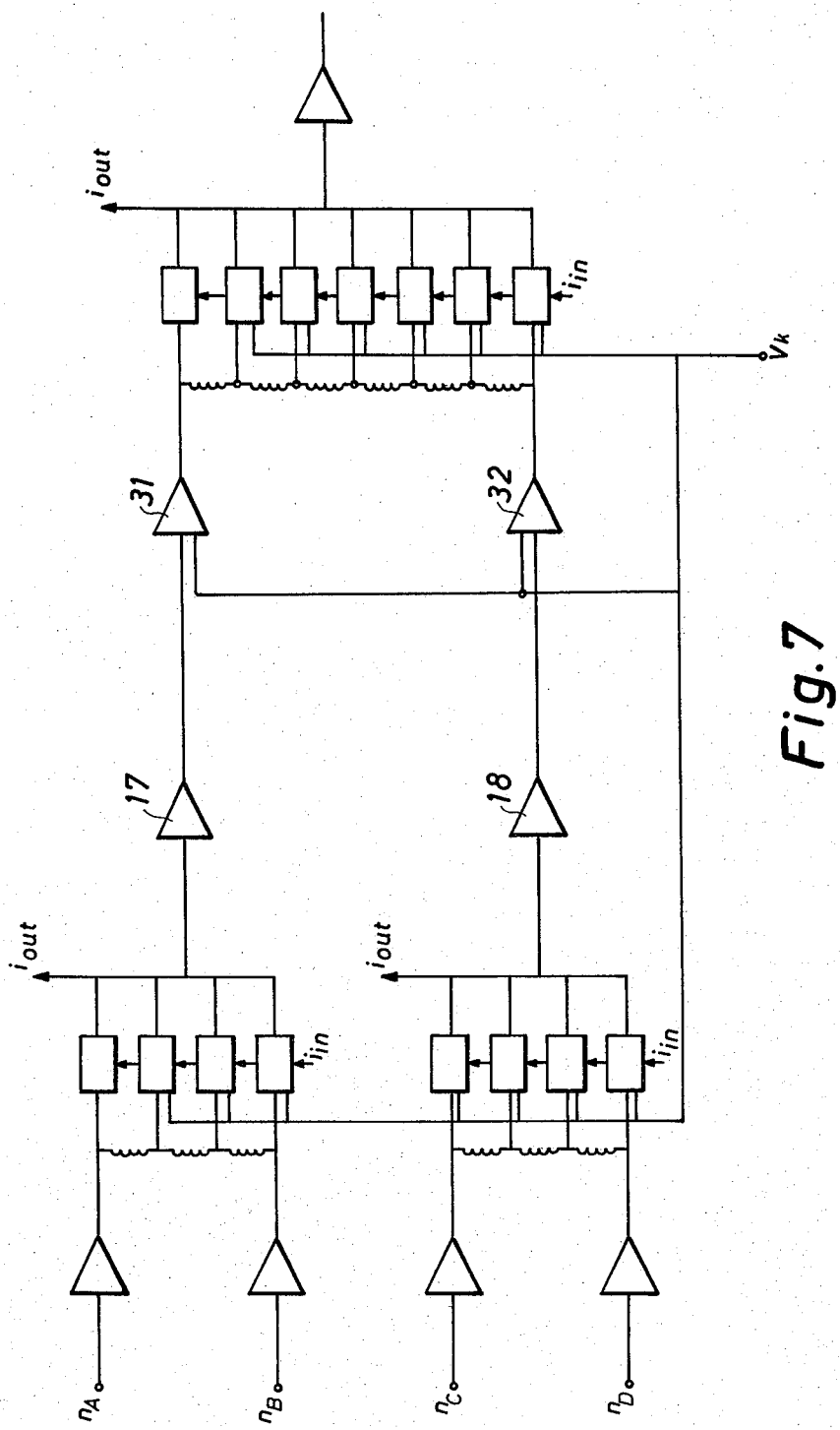

The invention will be described below with reference to the accompanying drawing, in which FIG. 1 illustrates the geometric relations during transmission of ultrasonic energy, p FIG. 2 illustrates the wave front of the transmitted waves, FIG. 3 illustrates the geometric relations of the received reflected waves, FIG. 4 illustrates the apparatus for controlling the ultrasonic transducers, and which comprises a plurality of uniformly constructed circuits, FIG. 5 illustrates an analog memory forming part of each circuit, FIG. 6 illustrates a phase-summation circuit forming part of the circuit shown in FIG. 4, and FIG. 7 illustrates a composite phase-summation circuit adapted to more than two transducer elements.

The apparatus illustrated in FIG. 4 for the control of the transducer elements in a row of equidistantly arranged ultrasonic transducer elements renders it possible to perform an angular and/or linear scanning of for instance a particular volume of tissue. The scanned area is reproduced for instance on an oscilloscope. In the case of reflection, an intensity modulation takes place in the point in question of the oscilloscope screen. Fast as well as slow scannings may be performed. It is an advantage to start with fast scannings until the more interesting regions of the volume have been located, whereafter the finer scannings which are slower may be performed. The apparatus may for instance be used for doctors requiring an examination of a specific region of tissue without involving a surgical intervention. The measuring transducer elements should not, of course, take up much room and the apparatus must besides be easy to handle. A further requirement is that the apparatus should be simple, and partly in order to facilitate use of the apparatus and partly in order to enable manufacture at a reasonable price.

The apparatus according to the invention is composed of uniform modules. Each module is a circuit mounted on its own circuit cord and controlling a set of transducer elements, said circuit comprising an analog memory 1 in connection with an analog calculating circuit 2. The latter controls in the first place the excitation of the two transducer elements in such manner that the transmitted ultrasonic waves focus in a predetermined point. FIG. 1 illustrates the geometric relations in relation to a reference unit C.

Approximated calculations imply that the delay of the excitation multiplied with the velocity of distribution instead of the formula of FIG. 1 may be $$-2x = -b(2a \sine \theta - b/2a - b \sine \theta).$$

This formula is used by time-coordination for signals received after a predetermined time from the distance a, since b is the distance (with signs) from the reference unit C, cf. FIG. 3. Delays of this magnitude provide a focusing in the illustrated focal point. The focal point is, of course, changed during the scanning. The change is performed from the outside by varying some parameter values in time with an adjustable frequency.

It now appears that a reflecting object is present in the actual focal point. Subsequently, the question is how to register said reflection in the best possible manner. This registration is, however, rather simple since the analog memory 1 performs a recording a predetermined time (equal to 13 μsec. minus a calculated delay after the element in question has received the reflected energy. Again the correction is the extra time (calculated with signs) necessary for the reflected energy to reach the element A at the distance b from the reference unit C. The analog memory is composed of 64 capacitors sampling the recorded signal (the reflected signal). The sampling procedure is performed by means of a recording-shift register, the 64 outputs of which are connected to control electrodes of field-effect transistors controlling the charging of the capacitors to the actual voltage of the input signal.

The collecting procedure is performed with a register shift frequency 2 to 3 times the signal frequency (i.e. about 5 MHz since the signal frequency is about 2 MHz), which is sufficient for recreating the recorded signal for instance by means of an envelope detector 4. In the case where the input received by the analog memory 1 is in the form of the curve designated "input signal" in FIG. 5, the output provided by the memory 1 is in the form designated "output signal" and the output of the envelope detector 4 is in the form designated "filtered signal". The signals recorded in the memories 1 are subsequently reproduced a predetermined time after excitation of the reference unit C. In case of reflection from the above focal point, the signals from all the envelope detectors 4 are in phase. A summation circuit 12 connected to all the envelope detectors provides thereby a relatively high signal at the moment in question. This signal is used for intensity modulation in an oscilloscope 13 simultaneously visualizing the scannings.

The input parameters comprise fixed parameter values and variable parameter values. The fixed parameter value is the value b which is characteristic for the circuit card in question, and which is provided by connecting the b-terminals mutually through resistors 10 of one and the same value. As a result a voltage divider is formed. This voltage divider is only to be supplied with a constant voltage. The second input parameter is the value $2a \sin \theta$, which varies partly in step with variations in the transmission direction from the reference unit C and partly in step with variations in the distance a from the reference unit C. The third input parameter is the value $2a$, and the fourth input parameter is the value $b \sin \theta$. The latter input parameter is also provided by connecting the terminals through resistors 21 of one and the same value, said resistors providing a voltage divider.

In order to limit the size of the apparatus, each circuit controls the excitation of two ultrasonic transducer elements through an interpolation circuit. The latter is composed of a voltage divider network 14, 15 and 16 mutually connecting the Y-terminals of succeeding circuits. Two of the circuit points of the voltage divider network are individually connected to the input of respective comparators 5 and 6 cf. FIG. 4. A ramp voltage is applied to the other terminals of the comparators in such manner that the two Y-values are converted to the two instants at which the two transducer elements respectively are to be activated, whereby each transducer element is punctually activated. The adjustment of the moment for the recording in the analog memory 1 is performed by means of a particular input control circuit 8. The latter is controlled and delayed by the analog calculating circuit 2 (calculating the delay) through a feedback loop comprising a pulse counter 20. The analog output signal of this pulse counter 20 is compared with the output signal of the calculating circuit for the control of a voltage controlled oscillator The VCO commences oscillating at a frequency determined by the calculated delay. This frequency is compared with a fixed read out frequency. As long as a difference exists between these two frequencies, the counter 20 counts the output signal which is linearly increasing in time. This output signal is subtracted from the voltage supplied to the VCO. When the VCO reaches a frequency corresponding to the read out frequency, the control unit 8 is activated, and the read in starts. As a result, the delay of the read in corresponds to the calculated delay.

In the above circuit the recording in the analog memory 1 for the element A takes place at a delay corresponding to a distance of propagation of 2 x, whereas the moment of reproducing is constant relative to the moment of excitation of the reference element C. Nothing, however, prevents the recording from being performed at an instant having a delay constant relative to the instant of excitation of C, and the instant of reproduction from being regulated instead.

Nor does anything prevent one and the same circuit from controlling the excitation of three or more transducer elements, whereby said circuit in that case combines the signals received by the three transducer elements into one signal. As a result the delay circuit may be less expensive. However, the quality is reduced too unless the phase combination is made ideal.

The apparatus may comprise an arbitrary number of transducer elements provided that a corresponding number of control circuit cards are present, preferably the same number of control circuit cards as transducer elements. In one embodiment 32 transducer elements and 16 control cards (each is illustrated in FIG. 4) are present.

In a particularly preferred embodiment of the apparatus each module is constructed in such manner that it is able to treat the signals from more than two transducer elements. The signals from two transducer elements are combined into a single signal by means of a phase-summation circuit of a first type, and the outputs of two phase-summation circuits of a first type are connected to a phase-summation circuit of a second type, cf. FIG. 7. As a result each module is able to treat signals from four transducer elements. In principle nothing, however, prevents said module from treating signals from 8, 16 or 64 transducer elements. Each phase-summation circuit is composed of a delay line in connection with a plurality of cascode amplifiers $A_1$, $A_2$, $A_3$, and $A_4$ whereby the outputs of the delay line are connected to their respective amplifier, cf. FIG. 7.

As illustrated in FIG. 6, the signals $V_{SA}$ and $V_{SB}$ are transmitted from the pre-amplifiers of two adjacent elements A and B to their respective end of a three-stage-LC-delay line. Each stage or link delays a quarter of a period at 2 MHz in such manner that for instance the signal $V_{SA}$ on the outputs $V_{S1}$, $V_{S2}$, $V_{S3}$, $V_{S4}$ is delayed O, $\frac{1}{4}$, $\frac{1}{2}$, and $\frac{3}{4}$ of a period respectively whereas the signal $V_{SB}$ on the same outputs is delayed $\frac{3}{4}$, $\frac{1}{2}$, $\frac{1}{4}$, and 0 of a period respectively. For instance, where a signal which was received by the element A a quarter of a period before it is received by the element B, both signals are present in the output $V_{S3}$ one quarter of a period after the signal is received by the element. This means that the signal present in the direction ARC sine $0.25 = 14.4°$ from the perpendicular (0°) is particularly emphasized at the output $V_{S3}$. This follows from the fact that the distance which the signal received by the element A has yet to travel before reaching the element B (i.e. one quarter of a wavelength), divided by the distance between the elements A and B, is equal to 0.25 (the sine of the angle of incidence). Therefore, the distance between the elements A and B is equal to one wavelength of ultrasound at the excitation frequency in the medium under investigation. The signals present in the direction ARC sine $0.75 = 49°$ are particularly emphasized at the output in $V_{S1}$ or $V_{S4}$. When the signals are received simultaneously by $V_{SA}$ and $V_{SB}$, these signals are summed with a 90° relative phase displacement both in $V_{S2}$ and $V_{S3}$. At the same time the summed values $V_{S2}$ and $V_{S3}$ are mutually in phase. As a result these values may be summed after introduction of appropriate multiplication factors. Since each voltage corresponds to a sum of two signals with a 90° phase displacement, the relative signal amplitude at both outputs $V_{S2}$ and $V_{S3}$ is $\sqrt{2}/2$. The sum $V_0 = 0.7\ V_{S2} + 0.7\ V_{S3}$ then possesses the relative amplitude 1. Corresponding calculations may be made with other multiplication factors for other angles in the range from $-49°$ to $+49°$. The succeeding circuit determines the factors by means of a voltage $V_K$ proportional to sine for the angle of incidence and applied to the emitter of a transistor forming part of each of the amplifiers $A_1$ to $A_4$.

$A_1$ to $A_4$ are cascode amplifiers having a differential output stage distributing the transmitting current to two branches in response to the basis voltage $V_{BB}$. One of these branches goes to the signal output $V_S$ and the second branch supplies the working current by feeding the signal in $C_f$ to the next amplifier A which is more positively biased. The reference voltages $V_{ref1}$, $V_{ref2}$, and $V_{ref3}$ are determined by the voltage area for $V_K$ and are symmetrically applied about OV. In the following the voltages are referred to as $-c$, 0, $+c$. $V_{b1}$ to $V_{b4}$ are appropriate working voltages distributed between $+c$ and $-c$. $C_s$ and $R_s$ are voltage transmission lines. When the angle of incidence $\phi$ is 0°, $V_K$ is OV. The working current $I_W$ is transmitted to $A_2$ as a result of the positive value of $V_K$ relative to $V_{ref1}$. Since $V_{BB2}$ is OV, $I_2$ is evenly distributed in the two branches $I_{2A}$ and $I_{2B}$. $I_{2A}$ thereby contains half the signal from $V_{S2}$ and is transmitted to the output $V_S \cdot I_{2B}$ is the half of the nominal working current fed to $A_3$ as $I_3$. Since $V_{BB3}$ is negative, $I_3$ is transmitted together with the signal $V_{S3}$ from the branch $I_{3A}$ to summation with $V_{S2} \cdot I_{3B}$ is 0. As a result the signal $V_{S4}$ cannot pass. In this case the amplified sum $V_S$ does not correspond to the desired amplified sum $V_0 = 0.7\ V_{S2}\ 0.7\ V_{S3}$, since $V_{S2}$ is only represented as $0.5\ V_{S2}$, and since $I_3 = 0.5\ I_W$ not necessarily implies a significant amplification reduction. By displacing $V_K$ somewhat in negative direction the representation 0.7 $V_{S2}$ and $I_3 = 0.3\ I_W$ is obtained. An appropriately low value of $I_W$ implies that $0.7\ V_{S3}$ is represented by $0.3\ I_W$. If $V_K$ is changed $+c/2$ from the previous value, the voltage distribution must be of such a magnitude that $I_{3A}$ exactly obtains a maximum value, since $I_{2A}$ is almost 0 when $I_{3B}$ increases. The ratio of $R_1$ to $R_2$ thus determines the uniformity of the phase summation. With $V_K = c$, $V_{S3}$ and $V_{S4}$ are summed as $V_{S2}$ and $V_{S3}$ with $V_K = 0$. With $V_K \geq 1.5e, I_{3B} = I_{432}\ I_W$. The $V_S$-output then only comprises $V_{S4}$. When $V_K \leq 1.5e$, $V_{S1}$ is only represented in $V_S$ and $A_2$. $A_3$ and $A_4$ are inactive since the working current thereof is 0.

The principle may be developed so as to include more links, cf. FIG. 7, wherein two circuits as described above individually sum up the signals from two elements A+B and C+D. After signal level coordination with logarithmic amplifiers 17, 18, a summation is performed by means of a second phase-summation circuit, the delay line of which, however, being more finely divided. The latter phase-summation circuit is also controlled by $V_K$.

An amplifier 30 connected to the output of the latter phase-summation circuit serves as activator for an analog memory.

The latter phase-summation circuit is not ideal in the sense that each link of the delay line has not the attenuation 0. It is possible to compensate therefor by amplifying the signals transmitted to the ends of the delay line, since the signal having the longest distance of transmission then obtains the greatest amplification by means of the amplifiers 31 and 32. Also the latter amplifications may be controlled by the voltage $V_K$.

The individual links of the delay line are composed of a coil in connection with a capacitor. However, for the sake of clearness FIG. 7 does not include these capacitors.

The apparatus according to the invention may be varied in many ways without deviating from the scope of the invention.

We claim:

1. An ultrasonic apparatus for producing a sectional view of an object on a screen, said apparatus comprising:
   (A) a plurality of like sets of at least two ultrasonic transducer elements each; and
   (B) a plurality of control units, each control unit being coupled to a respective one of said sets and including an analog calculating circuit arranged to excite the ultrasonic elements of the set in timed sequence to transmit ultrasonic energy focused at a respective common focal point in a region to be scanned, the common focal point of transmitted energy from each set being at a different position in said region, each said control unit further including means for combining echo signals produced by its associated set of transducer elements upon reception of reflected ultrasonic energy from an object in said region and an analog memory for delaying the combined signal so that it may be visually reproduced on said screen in a correct geometrical position relative to the combined signals respectively produced by the other sets of transducer elements, said echo signal combining means and analog memory being connected in controlled relation to said analog calculating circuit.

2. Ultrasonic apparatus for producing a sectional view of an object on a screen using a plurality of ultrasonic transducer elements, said apparatus comprising a timer (5,6) for timing the excitation of said transducer elements to produce a plurality of ultrasonic waves having a focal point adjacent which the object is to be placed, means for controlling said timer by voltages supplied thereto to cause the focal point to scan an area of the object, means (1,8) for coordinating the delays of the transducer element signals due to ultrasonic waves reflected from the object so as to synchronize and superpose said signals, and means (12,13) for displaying the reflected and superposed signals on a screen at a point corresponding to the focal point, said coordinating means including a plurality of uniformly constructed circuits (FIG. 4) each of which comprises an analog circuit (2) for calculating a voltage representing the delay of the instant of excitation of an associated transducer element from a voltage representing the spacing from a reference transducer element of the associated transducer elements and from voltages representing the position of the focal point with respect to the associated and reference transducer elements, said calculated analog voltages further controlling the delay of a signal due to a reflected ultrasonic wave received by the associated transducer element so that the signals received by all the transducer elements are superposed and displayed on the screen.

3. Ultrasonic apparatus according to claim 2, wherein said coordinating means comprises an analog memory and means for controlling the instants of input and output of the memory.

4. Ultrasonic apparatus according to claim 3, wherein said analog memory comprises 64 capacitors for storing sampled values of the reflected signals at 64 equidistant instants.

5. Ultrasonic apparatus according to claim 4, wherein a shift register (8) is provided for controlling the sampling of the reflected signals.

6. Ultrasonic apparatus according to claim 2, comprising a circuit (9) for combining signals received by two adjacent transducer elements into a single signal.

* * * * *